(12) United States Patent
Merrill, Jr. et al.

(10) Patent No.: US 9,651,473 B2
(45) Date of Patent: May 16, 2017

(54) WAFER LEVEL CENTRIFUGE FOR MEMS STICTION DETECTION AND SCREENING SYSTEM AND METHOD

(71) Applicant: mCube Inc., San Jose, CA (US)

(72) Inventors: Raymond Merrill, Jr., San Jose, CA (US); David Paul Jensen, San Jose, CA (US)

(73) Assignee: mCube Inc., San Jose, CA (US)

( * ) Notice: Subject to any disclaimer, the term of this patent is extended or adjusted under 35 U.S.C. 154(b) by 294 days.

(21) Appl. No.: 14/222,575

(22) Filed: Mar. 21, 2014

(65) Prior Publication Data
US 2014/0290331 A1    Oct. 2, 2014

Related U.S. Application Data

(60) Provisional application No. 61/805,445, filed on Mar. 26, 2013, provisional application No. 61/829,034, filed on May 30, 2013, provisional application No. 61/820,123, filed on May 6, 2013.

(51) Int. Cl.
*G01N 19/02*    (2006.01)
*B81C 99/00*    (2010.01)

(52) U.S. Cl.
CPC ........... *G01N 19/02* (2013.01); *B81C 99/005* (2013.01)

(58) Field of Classification Search
USPC ........................ 73/1.38, 460, 514.01, 514.02
See application file for complete search history.

(56) References Cited

U.S. PATENT DOCUMENTS

| 5,389,182 | A | 2/1995 | Mignardi et al. |
| 6,445,203 | B1 | 9/2002 | Yamashita et al. |
| 8,637,943 | B1* | 1/2014 | Yang .................... B81C 1/0023 257/252 |
| 2009/0095095 | A1* | 4/2009 | Hayashi ................ B81C 99/005 73/865.8 |

(Continued)

FOREIGN PATENT DOCUMENTS

| CN | 104069955 | 10/2014 |
| TW | 201500115 | 1/2015 |

OTHER PUBLICATIONS

U.S. Appl. No. 14/267,864, "Non Final Office Action", Jan. 12, 2017.

(Continued)

*Primary Examiner* — Eric S McCall
(74) *Attorney, Agent, or Firm* — Kilpatrick Townsend & Stockton LLP (57) ABSTRACT

A wafer level centrifuge (WLC) system and method of testing MEMS devices using the system. The wafer level centrifuge (WLC) system can include a base centrifuge system and a cassette mounting hub coupled to the base centrifuge system. The method can include applying a smooth and continuous acceleration profile to two or more MEMS wafers via the base centrifuge system. Each of the two or more MEMS wafers can have one or more MEMS devices formed thereon. The two or more MEMS wafers can be provided in two or more wafer holding cassettes configured on the cassette mounting hub. The method can also include identifying one or more target MEMS wafers, which can include identifying stiction in one or more MEMS devices on the one or more MEMS wafers.

18 Claims, 6 Drawing Sheets

(56) References Cited

U.S. PATENT DOCUMENTS

| | | |
|---|---|---|
| 2011/0156734 A1 | 6/2011 | Berry et al. |
| 2011/0260734 A1 | 10/2011 | Liao et al. |
| 2012/0304926 A1 | 12/2012 | Boguslavskiy et al. |
| 2014/0352403 A1* | 12/2014 | Merrill, Jr. ............. G01N 19/02 73/9 |
| 2015/0284245 A1* | 10/2015 | Merrill, Jr. ............ B81C 99/005 73/865.9 |

OTHER PUBLICATIONS

U.S. Appl. No. 14/267,864, "Restriction Requirement", Oct. 19, 2016, 7 pages.

* cited by examiner

FIG. 8

WAFER LEVEL CENTRIFUGE FOR MEMS STICTION DETECTION AND SCREENING SYSTEM AND METHOD

CROSS-REFERENCES TO RELATED APPLICATIONS

The present application claims priority to and incorporates by reference, for all purposes, the following provisional patent application: U.S. Provisional App. 61/805,445, filed Mar. 26, 2013; U.S. Provisional App. 61/829,034, filed May 30, 2013; and U.S. Provisional App. 61/820,123, filed May 6, 2013.

BACKGROUND OF THE INVENTION

The present invention is directed to MEMS (Micro-Electro-Mechanical-Systems). More specifically, embodiments of the invention provide methods and systems for testing wafer level MEMS devices, including inertial sensors and the like.

Research and development in integrated microelectronics have continued to produce astounding progress in CMOS and MEMS. CMOS technology has become the predominant fabrication technology for integrated circuits (IC). MEMS, however, continues to rely upon conventional process technologies. In layman's terms, microelectronic ICs are the "brains" of an integrated device which provides decision-making capabilities, whereas MEMS are the "eyes" and "arms" that provide the ability to sense and control the environment. Some examples of the widespread application of these technologies are the switches in radio frequency (RF) antenna systems, such as those in the iPhone™ device by Apple, Inc. of Cupertino, Calif., and the Blackberry™ phone by Research In Motion Limited of Waterloo, Ontario, Canada, and accelerometers in sensor-equipped game devices, such as those in the Wii™ controller manufactured by Nintendo Company Limited of Japan. Though they are not always easily identifiable, these technologies are becoming ever more prevalent in society every day.

Beyond consumer electronics, use of IC and MEMS has limitless applications through modular measurement devices such as accelerometers, gyroscopes, actuators, and sensors. In conventional vehicles, accelerometers and gyroscopes are used to deploy airbags and trigger dynamic stability control functions, respectively. MEMS gyroscopes can also be used for image stabilization systems in video and still cameras, and automatic steering systems in airplanes and torpedoes. Biological MEMS (Bio-MEMS) implement biosensors and chemical sensors for Lab-On-Chip applications, which integrate one or more laboratory functions on a single millimeter-sized chip only. Other applications include Internet and telephone networks, security and financial applications, and health care and medical systems. As described previously, ICs and MEMS can be used to practically engage in various type of environmental interaction.

Although highly successful, ICs and in particular MEMS still have limitations. Similar to IC development, MEMS development, which focuses on increasing performance, reducing size, and decreasing cost, continues to be challenging. Additionally, applications of MEMS often require increasingly complex microsystems that desire greater computational power. Unfortunately, such applications generally do not exist. These and other limitations of conventional MEMS and ICs may be further described throughout the present specification and more particularly below.

From the above, it is seen that techniques for improving the manufacture of integrated circuit devices and MEMS are highly desired.

BRIEF SUMMARY OF THE INVENTION

The present invention is directed to MEMS (Micro-Electro-Mechanical-Systems). More specifically, embodiments of the invention provide methods and systems for testing wafer level MEMS devices. Merely by way of example, the MEMS device can include at least an accelerometer, a gyroscope, a magnetic sensor, a pressure sensor, a microphone, a humidity sensor, a temperature sensor, a chemical sensor, a biosensor, an inertial sensor, and others. But it will be recognized that the invention has a much broader range of applicability.

Embodiments of the present invention can include a wafer level centrifuge (WLC) system and method of testing MEMS devices using the system. The wafer level centrifuge (WLC) system can include a base centrifuge system and a cassette mounting hub coupled to the base centrifuge system. The method can include applying a smooth and continuous acceleration profile to two or more MEMS wafers via the base centrifuge system. Each of the two or more MEMS wafers can have one or more MEMS devices formed thereon. The two or more MEMS wafers can be provided in two or more wafer holding cassettes configured on the cassette mounting hub. The method can also include identifying one or more target MEMS wafers, which can include identifying stiction in one or more MEMS devices on the one or more MEMS wafers.

Wafer Centrifuge or Wafer Level Centrifuge (WLC) provides a continuous, non-destructive way to expose all of the MEMS devices on a silicon wafer to g-forces high enough to cause contact between moving parts. If any given die on the wafer remains stuck after the g-force is removed, the die can then be detected by chip probe and removed from the product population.

Various additional objects, features and advantages of the present invention can be more fully appreciated with reference to the detailed description and accompanying drawings that follow.

BRIEF DESCRIPTION OF THE DRAWINGS

In order to more fully understand the present invention, reference is made to the accompanying drawings. Understanding that these drawings are not to be considered limitations in the scope of the invention, the presently described embodiments and the presently understood best mode of the invention are described with additional detail through use of the accompanying drawings in which.

DETAILED DESCRIPTION OF THE INVENTION

The present invention is directed to MEMS (Micro-Electro-Mechanical-Systems). More specifically, embodiments of the invention provide methods and structures for improving integrated MEMS devices, including inertial sensors and the like. Merely by way of example, the MEMS device can include at least an accelerometer, a gyroscope, a magnetic sensor, a pressure sensor, a microphone, a humidity sensor, a temperature sensor, a chemical sensor, a biosensor, an inertial sensor, and others. But it will be recognized that the invention has a much broader range of applicability.

Embodiments of the present invention provide a remedy for stimulating MEMS contact in a controlled way so as to detect and possibly screen MEMS devices in wafer form for stiction.

In many MEMS devices, silicon structures are either designed to move, or move as a secondary effect, as the result of a given acceleration, and come into contact with another surface as the end of travel is reached. The problem is that typical methods of stimulating a MEMS device to reach the point of contact involve shocking devices mechanically. These methods would not be possible in wafer form, nor would these methods be very repeatable given the complex dynamics of shock testing.

Wafer Centrifuge or Wafer Level Centrifuge (WLC) provides a continuous, non-destructive way to expose all of the MEMS devices on a silicon wafer to g-forces high enough to cause contact between moving parts. If any given die on the wafer remains stuck after the g-force is removed, the die can then be detected by chip probe and removed from the product population.

The alternative is packaged part shock testing or centrifuge, which is far more costly and time consuming.

Figure 1:
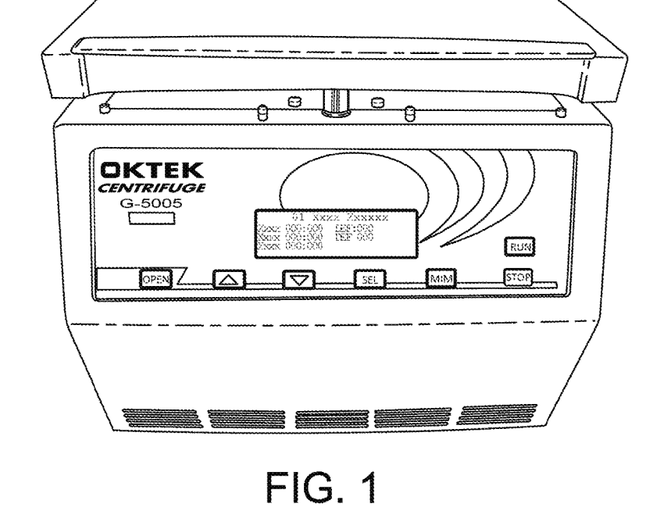
FIG. 1 is a picture of a conventional centrifuge.

FIG. 1 is a picture of a conventional centrifuge. This centrifuge is an OKTEK model G-5005. Embodiments of the present invention can include such a centrifuge with custom hardware designed to provide a unique platform for exposing up to four 8" wafers to a rotational centrifugal force (RCF). Other off-the-shelf centrifuge models and the like can be used in the WLC systems as described herein. These WLC systems can be designed for ease of use and safety. For example, retrofitting an existing centrifuge can be time-efficient and may only require a Phillips head screwdriver.

Figure 2:
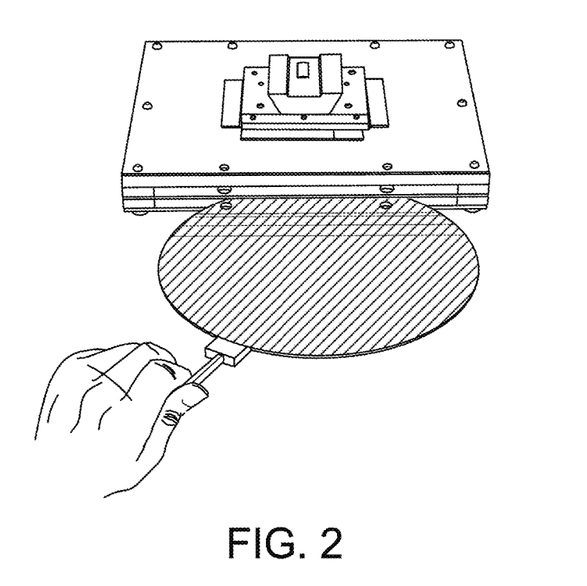
FIG. 2 is a picture of a conventional wafer holding cassette with a wafer.

FIG. 2 is a picture of a conventional wafer holding cassette with a wafer. This wafer holding cassette is a 2-slot titanium wafer cassette with Delrin ribs for wafer edge protection. These wafer holding cassettes can be used in one or more embodiments of the WLC system.

Figure 3:
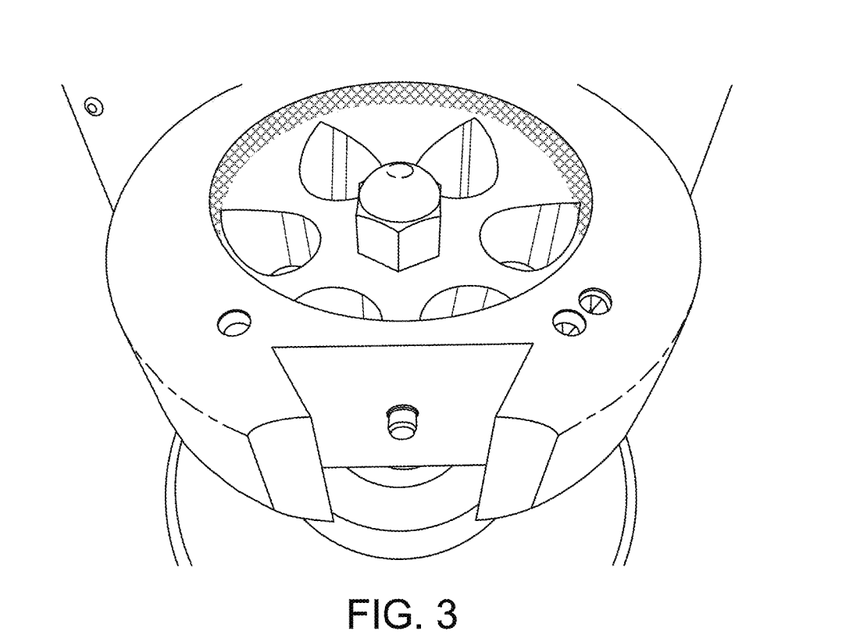
FIG. 3 is a picture of a conventional dovetail central hub.

FIG. 3 is a picture of a conventional dovetail central hub. This central hub can be a pinned dovetail central hub, which can be used in one or more embodiments of the WLC system. These kinds of dovetail central hubs can provide quick cassette insertion and removal, which allows ease of operation and minimal risk of operator installation error.

Other similar mechanisms that releasably secure the cassettes to the drive hub can be used in place of the dovetail hub as well.

Figure 4:
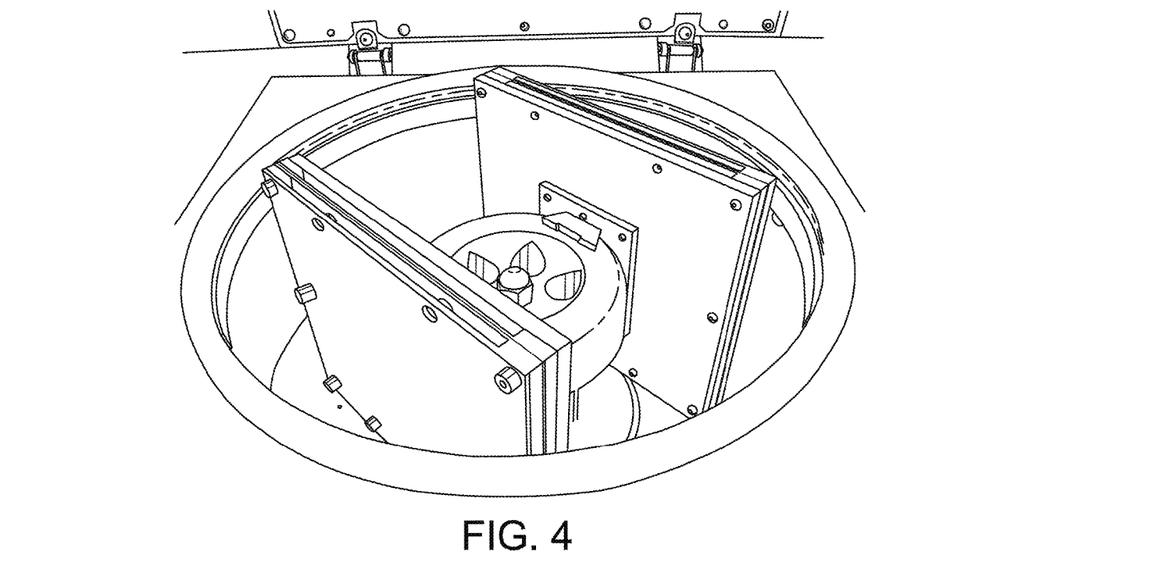
FIG. 4 is a picture of a Wafer Level Centrifuge (WLC) system according to an embodiment of the present invention.

FIG. 4 is a picture of a Wafer Level Centrifuge (WLC) system according to an embodiment of the present invention. Here, two wafer holding cassettes are configured in a vertical manner on a central dovetail hub coupled to a base centrifuge. The hub and cassettes can be precision balanced at fabrication.

In a specific embodiment, the wafers are loaded with the top (bond pad side) facing the dove tail mounting bracket. This will orient the g-force in the +Z direction with regard to the MEMS devices on the wafers. Each side of the WLC system needs to be matched with the same number of wafers to ensure proper balancing. Failure to balance the components properly can be a safety hazard. The spinning wafers should involve either 2 or 4 wafers, or an even number of wafers to ensure balance.

Figure 5:
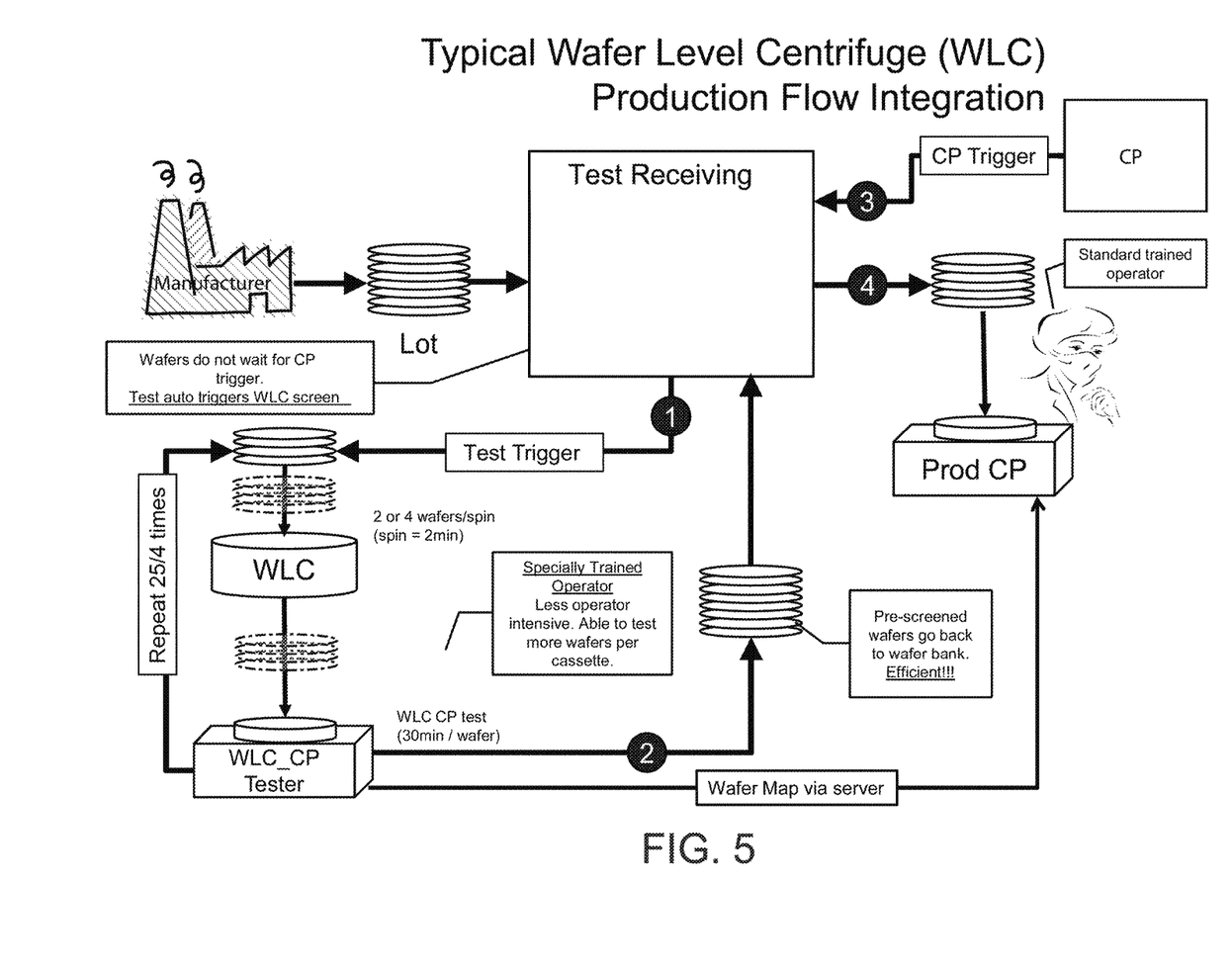
FIG. 5 is a simplified diagram illustrating a method of fabricating a MEMS device using WLC testing according to an embodiment of the present invention.

FIG. 5 is a simplified diagram illustrating a method of fabricating a MEMS device using WLC testing according to an embodiment of the present invention. This diagram shows a manufacturer providing a lot of wafers, which can be MEMS wafers having one or more MEMS devices formed thereon, to a test receiving plant. As marked by path 1, a test trigger can initiate the WLC testing process, which is independent of the CP trigger marked by path 3. The wafers that pass the WLC testing/screening process, in path 2 are then developed into a fully packaged product, as marked by path 4.

Embodiments of the methodology may include some or all of the steps:

Inserting one or more wafers into one or more wafer holding cassettes. The wafer holding cassettes may be preinstalled into the centrifuge or installed after the wafers are inserted therein.

Applying a controlled (programmed profile, e.g. smooth, continuous, step, pulsed, etc.) acceleration profile to silicon wafers.

Removing the one or more wafers from the cassettes (before or after the cassettes are removed from the centrifuge).

Integrating this stimulus method into a wafer probe production flow, e.g. determining which MEMS devices at the wafer level have/do not have stiction problems, and separating MEMS devices from the wafer that do not have stiction issues.

Figure 6:
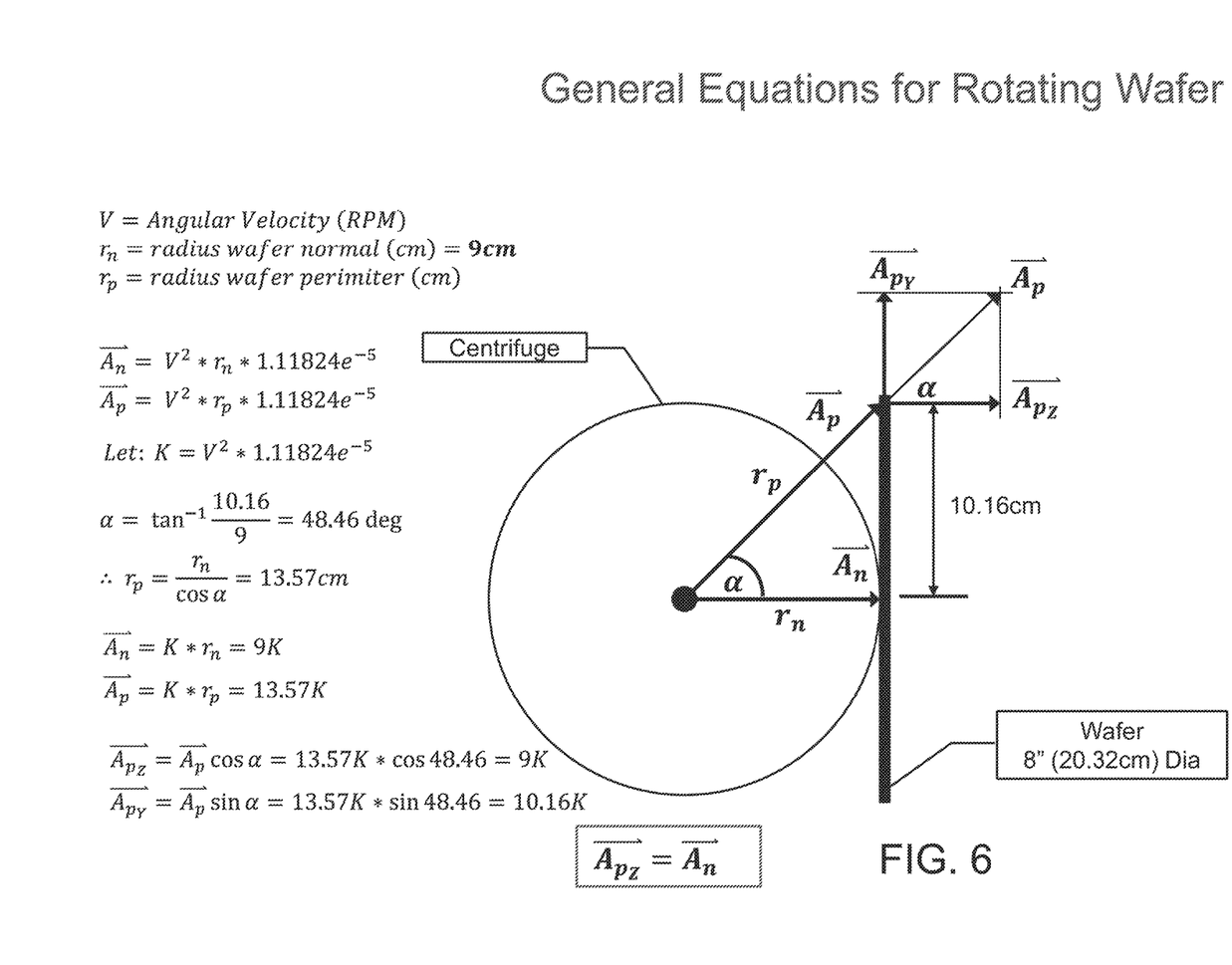
FIG. 6 is simplified diagram illustrating the forces acting on a wafer within a centrifuge according to an embodiment of the present invention.

FIG. 6 is simplified diagram illustrating the forces acting on a wafer within a centrifuge according to an embodiment of the present invention. These equations show that the force vectors $A_{pz}$ and $A_n$ are equal.

There is no different in the Z g-force vector between a die in the center of the wafer and a die at the edge.

$$\vec{A}_{pz} = \vec{A}_n$$

However, there is a big different in the Y g-forces. At wafer center, there is zero tangential force. At wafer edge, tangential force is 10.16K, which is 13% higher g-force that in the Z direction.

$$\vec{A}_{pz} = \vec{A}_p \cos \alpha = 13.57K * \cos 48.46 = 9K$$

$$\vec{A}_{py} = \vec{A}_p \sin \alpha = 13.57K * \sin 48.46 = 10.16K$$

The general equation for angular velocity given a desired g-force:

$$V = \sqrt{\frac{\vec{A_n}}{9*1.11824e^{-5}}}$$

Figure 7:
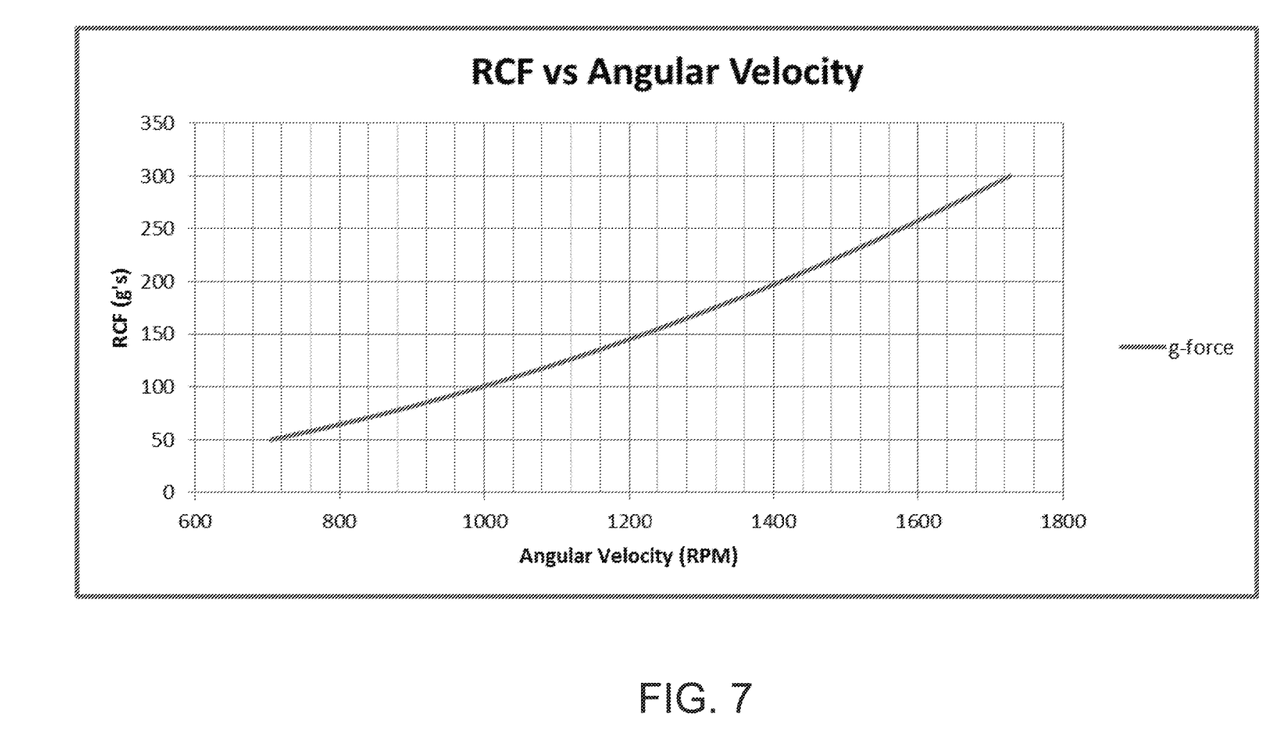
FIG. 7 is a simplified graph representing a rotational centrifugal force (RCF)—angular velocity relationship according to an embodiment of the present invention.

FIG. 7 is a simplified graph representing a rotational centrifugal force (RCF)—angular velocity relationship according to an embodiment of the present invention.

Figure 8:
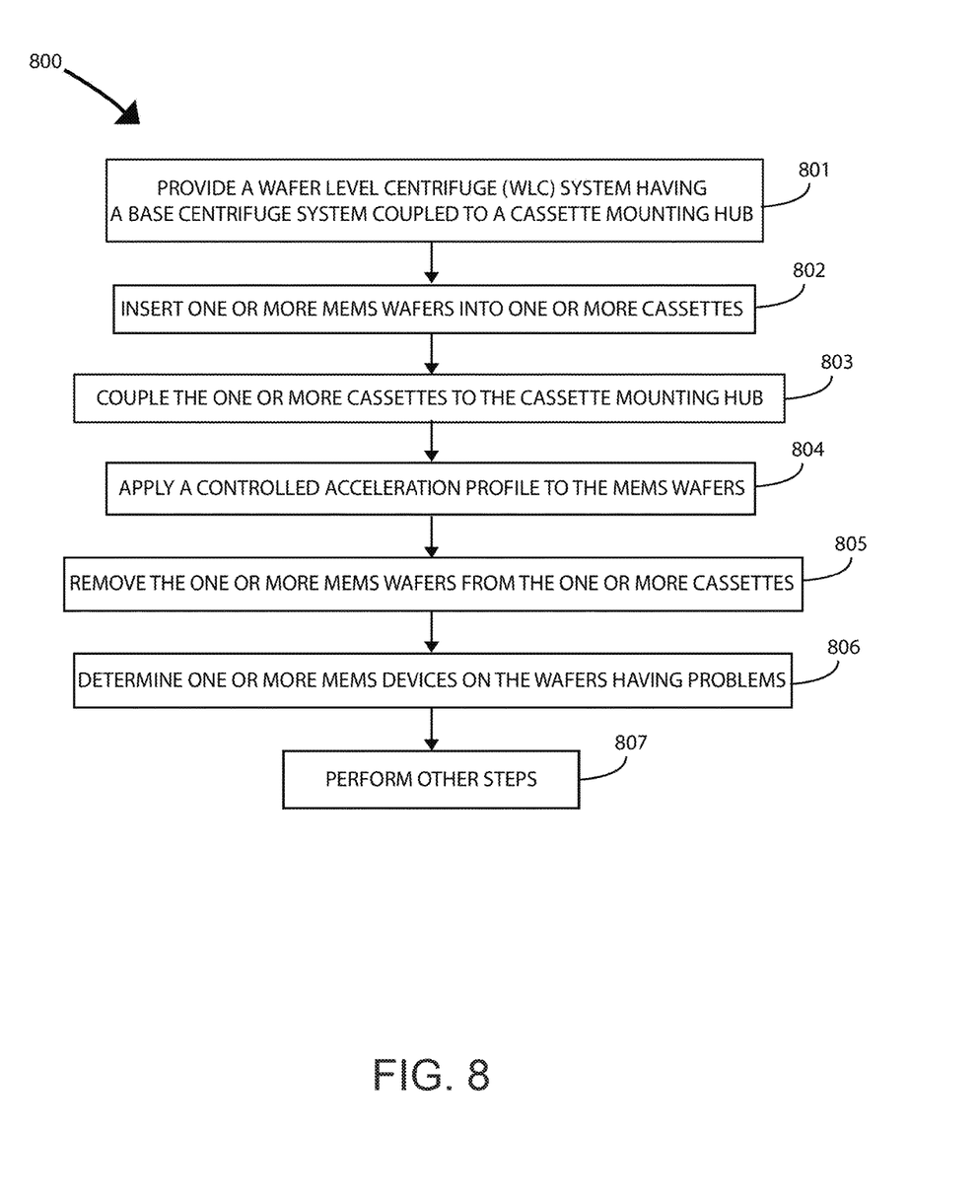
FIG. 8 is a simplified flow diagram illustrating a method for fabricating a MEMS device using a WLC system according to an embodiment of the present invention.

FIG. 8 is a simplified flow diagram illustrating a method for fabricating a MEMS device using a WLC system according to an embodiment of the present invention. This method uses the WLC system having a base centrifuge system coupled to a cassette mounting hub, as outlined below:
- 801. Provide a Wafer Level Centrifuge (WLC) system having a base centrifuge system coupled to a cassette mounting hub;
- 802. Insert one or more MEMS wafers into one or more cassettes;
- 803. Couple the one or more cassettes to the cassette mounting hub;
- 804. Apply a controlled acceleration profile to the MEMS wafers;
- 805. Remove the one or more MEMS wafers from the one or more cassettes;
- 806. Determine one or more MEMS devices on the wafers having physical problems; and
- 807. Perform other steps, as desired.

As shown, the present method has a sequence of steps, which can be varied, modified, replaced, reordered, expanded, contracted, or any combinations thereof. That is, the method repeats any of the above steps. Such steps may be performed alone or in combination with others, which are described or not even described. The steps can be performed in the order shown or in other orders, if desired. The steps also can be performed using a combination of hardware and software using other process steps. The steps also can be performed using hardware or other processes implemented using software and the like. Of course, there can be many other variations, modifications, and alternatives. Further details of the present method can be found throughout the present specification and more particularly below.

In an embodiment, the present invention provides a method for testing MEMS devices using a WLC system. As shown in FIG. 8, the method can begin with providing a WLC system, step 801. One or more MEMS wafers, each having at least a MEMS device formed thereon, can be inserted into one or more cassettes, step 802. In a specific embodiment, the one or more wafers can include two or more wafers (even number of wafers) and can be inserted into two or more cassettes (even number of cassettes), which are configured in a precision balanced manner on the cassette mounting hub. Each of the MEMS wafers can include a top or bond pad side. These cassettes can be coupled to the cassette mounting hub of the WLC system, step 803. The MEMS wafers and cassettes can be configured such that the top side of each of the MEMS wafers faces the cassette mounting hub. The cassettes can be vertically or horizontally mounted on the cassette mounting hub.

Once in the WLC system, a controlled acceleration profile can be applied to the MEMS wafers via the WLC system, step 804. Following processing in the WLC system, the one or more MEMS wafers from the one or more cassettes, step 805. MEMS devices with physical problems on these wafers can then be identified, step 806. These physical problems can include stiction problems in the MEMS devices. Other steps can be additionally performed as necessary.

In an embodiment, the present invention can provide a method for testing MEMS devices using a wafer level centrifuge (WLC) system including a base centrifuge system and a cassette mounting hub coupled to the base centrifuge system. The method can include providing two or more MEMS wafers, each having one or more MEMS devices formed thereon. The two or more MEMS devices can be configured within two or more wafer holding cassettes. In an embodiment, there can be two or four MEMS wafers, each of which having one or more MEMS devices formed thereon.

These wafer holding cassettes can be configured on the cassette mounting hub. The cassettes can be 2-slot titanium wafer cassettes with Delrin ribs, but others can be used as well. In a specific embodiment, the MEMS wafers in the wafer holding cassettes can be configured in a precision balanced manner on the hub. The wafer holding cassettes can be vertically or horizontally mounted. The cassette mounting hub can include a pinned dovetail central cassette mounting hub.

In a specific embodiment, each of the two or more MEMS wafers includes a top or bond pad side. When mounting the MEMS wafers and wafer holding cassettes, the configuration can include positioning the MEMS wafers such that the top side of each wafer faces the cassette mounting hub from within the wafer holding cassettes. These wafer holding cassettes can also be configured such that the g-force from applying an acceleration profile is oriented in the Z+ direction relative to the one or more MEMS devices one each of the MEMS wafers.

A controlled acceleration profile can be applied to the MEMS wafers via the base centrifuge system, and one or more target MEMS wafers can be identified. The controlled acceleration profile can include a smooth acceleration profile, a continuous acceleration profile, a step-wise acceleration profile, a pulsed acceleration profile, or other profile. More specifically, one or more MEMS devices exhibiting stiction can be identified on the MEMS wafers. Various processes can be used in this identification process, including chip probing, wafer probing, conventional probe production, or the like and combinations thereof.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for testing MEMS devices using a wafer level centrifuge (WLC) system comprising a base centrifuge system and a cassette mounting hub coupled to the base centrifuge system, the method comprising:
    inserting one or more MEMS wafers into one or more cassettes;
    coupling the one or more cassettes to the cassette mounting hub;
    applying a controlled acceleration profile to the one or more MEMS wafers via the base centrifuge system, wherein each of the one or more MEMS wafers having one or more MEMS devices formed thereon;
    removing the one or more MEMS wafers from the one or more cassettes; and
    determining if the one or more MEMS devices from the one or more MEMS wafers has physical problems;
    wherein the one or more MEMS wafers and the one or more cassettes include two or more MEMS wafers and two or more cassettes configured in a precision balanced manner on the cassette mounting hub.

2. The method of claim 1 wherein each of the one or more MEMS wafers comprises a top or bond pad side, and wherein the one or more MEMS wafers and the one or more cassettes are configured such that the top side of each of the MEMS wafers faces the cassette mounting hub from within the one or more cassettes.

3. The method of claim 1 wherein the one or more cassettes are vertically mounted on the cassette mounting hub.

4. The method of claim 1 wherein the one or more cassettes are horizontally mounted on the cassette mounting hub.

5. A method for testing MEMS devices using a wafer level centrifuge (WLC) system comprising a base centrifuge system and a cassette mounting hub coupled to the base centrifuge system, the method comprising:
inserting one or more MEMS wafers into one or more cassettes;
coupling the one or more cassettes to the cassette mounting hub;
applying a controlled acceleration profile to the one or more MEMS wafers via the base centrifuge system, wherein each of the one or more MEMS wafers having one or more MEMS devices formed thereon;
removing the one or more MEMS wafers from the one or more cassettes; and
determining if the one or more MEMS devices from the one or more MEMS wafers has physical problems,
wherein the physical problems comprise stiction problems, wherein moving parts in a MEMS wafer remain stuck.

6. A method for testing MEMS devices using a wafer level centrifuge (WLC) system comprising a base centrifuge system and a cassette mounting hub coupled to the base centrifuge system, the method comprising:
providing two or more MEMS wafers, each having one or more MEMS devices formed thereon;
configuring the two or more MEMS wafers within two or more wafer holding cassettes;
configuring the two or more wafer holding cassettes on the cassette mounting hub;
applying a controlled acceleration profile to the MEMS wafers via the base centrifuge system; and
identifying one or more target MEMS wafers that have physical problems as a result of testing.

7. The method of claim 6 wherein the configuring of the two or more MEMS wafers and the two or more wafer holding cassettes are configured in a precision balanced manner on the cassette mounting hub.

8. The method of claim 6 wherein the two or more MEMS wafers comprises two or four MEMS wafers.

9. The method of claim 6 wherein each of the two or more MEMS wafers comprises a top or bond pad side, and wherein the configuring of the two or more MEMS wafers and the two or more wafer holding cassettes are such that the top side of each of the MEMS wafers faces the cassette mounting hub from within the two or more wafer holding cassettes.

10. The method of claim 6 wherein the configuring of the two or more MEM wafers and the two or more wafer holding cassettes is such that the g-force from applying the acceleration profile is oriented in the +Z direction relative to the one or more MEMS devices of each of the one or more MEMS wafers.

11. The method of claim 6 wherein the identifying of the one or more target MEMS wafers comprises identifying stiction in one or more MEMS devices on the one or more MEMS wafers.

12. The method of claim 6 wherein the identifying of the one or more target MEMS wafers comprises using a chip probing process, a wafer probing process, or convention wafer probe production process to identify the one or more target MEMS wafers.

13. The method of claim 6 wherein providing the two or more MEMS wafers comprises providing two or four MEMS wafers, each of the two or four MEMS wafers having one or more MEMS devices formed thereon.

14. The method of claim 6 wherein each of the two or more wafer holding cassettes comprise 2-slot Titanium wafer cassettes with Delrin ribs.

15. The method of claim 6 wherein the two or more wafer holding cassettes are vertically mounted on the cassette mounting hub.

16. The method of claim 6 wherein the two or more wafer holding cassettes are horizontally mounted on the cassette mounting hub.

17. The method of claim 6 wherein the cassette mounting hub comprises a pinned dovetail central cassette mounting hub.

18. The method of claim 6 wherein the controlled acceleration profile includes a smooth acceleration profile, a continuous acceleration profile, a step-wise acceleration profile, or a pulsed acceleration profile.

* * * * *